(12) United States Patent
Grassere et al.

(10) Patent No.: US 11,510,624 B2
(45) Date of Patent: Nov. 29, 2022

(54) WIRELESS VITAL SIGN MONITORING (71) Applicant: AGIS AUTOMATISERING BV, Harmelen (NL)

(72) Inventors: Stefanus Hendrikus Hubertina Grassere, Harmelen (NL); Joris Christian Beudel, Harmelen (NL); Maarten-Jan Van Fulpen, Harmelen (NL)

(73) Assignee: AGIS AUTOMATISERING BV

( * ) Notice: Subject to any disclaimer, the term of this patent is extended or adjusted under 35 U.S.C. 154(b) by 243 days.

(21) Appl. No.: 16/337,084

(22) PCT Filed: Sep. 27, 2017

(86) PCT No.: PCT/EP2017/074557
§ 371 (c)(1),
(2) Date: Mar. 27, 2019

(87) PCT Pub. No.: WO2018/060291
PCT Pub. Date: Apr. 5, 2018

(65) Prior Publication Data
US 2020/0029903 A1    Jan. 30, 2020

(30) Foreign Application Priority Data

Sep. 27, 2016 (NL) .................................. 2017538

(51) Int. Cl.
*A61B 5/00* (2006.01)
*A61B 5/11* (2006.01)
(52) U.S. Cl.
CPC .......... *A61B 5/6838* (2013.01); *A61B 5/0002* (2013.01); *A61B 5/1118* (2013.01);
(Continued)

(58) Field of Classification Search
CPC ... A61B 5/6838; A61B 5/0002; A61B 5/1118; A61B 5/6816; A61B 5/6843; A61B 5/721; A61B 5/02416
See application file for complete search history.

(56) References Cited

U.S. PATENT DOCUMENTS 7,406,180 B2    7/2008  Milde
2008/0319325 A1*  12/2008  Tatara .................. A61B 5/6817
                                                    600/480
(Continued)

FOREIGN PATENT DOCUMENTS

CN          1849843 A      10/2006
CN          101877995 A    11/2010
(Continued)

OTHER PUBLICATIONS

International Search Report and Written Opinion; dated Dec. 21, 2017 for PCT/EP2017/074557.
(Continued)

*Primary Examiner* — Sean P Dougherty
*Assistant Examiner* — Alexander H Connor
(74) *Attorney, Agent, or Firm* — Mendelsohn Dunleavy, P.C.

(57) ABSTRACT

A method of determining one or more vital sign parameters by a wireless vital-sign measurement device comprises: measuring motion information of a user wearing the wireless measurement device, the measurement device being in the idle mode in which at least one opto-electronic sensor in the measurement device is deactivated; switching the measurement device in an active mode if the motion information is below a predetermined threshold, wherein in the active mode the at least one opto-electronic sensor is activated; during a predetermined measuring period, exposing part of a skin tissue of the user to light and measuring one or more optical response signals associated with the exposed skin (Continued)

tissue and the motion sensor measuring motion information associated with movements of the user; and, selecting or rejecting one or more pulses in the one or more optical response signals on the basis of the motion information measured during the measuring period and determining one or more vital sign parameters on the basis of the one or more selected pulses.

6 Claims, 6 Drawing Sheets

(52) U.S. Cl.
CPC .......... *A61B 5/6816* (2013.01); *A61B 5/6843* (2013.01); *A61B 5/721* (2013.01); *A61B 2560/0209* (2013.01); *A61B 2562/0219* (2013.01)

(56) References Cited

U.S. PATENT DOCUMENTS

| | | |
|---|---|---|
| 2009/0119884 A1 | 5/2009 | Kitazawa |
| 2010/0152557 A1* | 6/2010 | Oh .................... A61B 5/6816 600/309 |
| 2010/0261981 A1 | 10/2010 | Griffioen |
| 2014/0155705 A1 | 6/2014 | Papadopolulos et al. |
| 2014/0355809 A1 | 12/2014 | Killion et al. |
| 2015/0157269 A1 | 6/2015 | Lisogurski et al. |
| 2015/0250418 A1 | 9/2015 | Ashby |
| 2015/0305689 A1 | 10/2015 | Gourmelon et al. |
| 2019/0167123 A1* | 6/2019 | Hidaka ................ A61B 5/0245 |

FOREIGN PATENT DOCUMENTS

| | | | |
|---|---|---|---|
| DE | 102008022919 A1 | 11/2009 | |
| EP | 2116183 A1 | 11/2009 | |
| EP | 2116183 B1 * | 11/2009 | .......... A61B 5/0245 |
| JP | 2008-43513 A | 2/2008 | |
| WO | WO2016113143 A1 | 7/2016 | |

OTHER PUBLICATIONS

First Examination Report for corresponding Chinese application No. 201780073284.9; dated Apr. 27, 2021 (21 pages) Machine Translation.

Second Office Action for corresponding Chinese application No. 201780073284.9; dated May 30, 2022 (17 pages) Machine Translation.

* cited by examiner

WIRELESS VITAL SIGN MONITORING

FIELD OF THE INVENTION

The invention relates to wireless vital sign monitoring, and, in particular, though not exclusively, to methods and systems for wireless vital sign monitoring, a measuring device adapted for wireless vital sign monitoring, and a computer program product for executing such methods.

BACKGROUND OF THE INVENTION

Currently in hospitals multiple vital signs of patients in high-care wards are being monitored continuously twenty-four hours a day. In contrast, when a patient is in a low-care hospital ward, only selected vital signs such as pulse, oxygen saturation (SpO2), and temperature are monitored and this is done manually at 6-8 hour time intervals using spot measurements (usually referred to as a spot check). Typically, the measurements are manually entered into a (electronic) patient dossier. Patient safety can be improved, while working more efficiently at the same time when an automated trend of multiple vital signs could be measured.

US2015/0305689 describes a system for automated spot checks wherein wireless measuring devices are configured to measure vital signs and an activity state (e.g. standing, sitting, walking, running, etc.) of a patient. The activity state allows the system to determine whether measured data belong to the same activity state so that the data can be compared in time. This way, the system may determine to change the measurement schedule e.g. increase the measurement frequency, in case the measured data show a degradation in time, e.g. increase in blood pressure when the patent is inactive.

In such low-care vital sign measurement small wireless wearable measuring devices are preferred, as the measuring devices should not restrict the mobility and movements of the patients. In order to make such monitoring devices practical useful, the energy consumption of the wireless measuring device should be optimized so that measurements can be performed over a substantial period of time, e.g. 24-48 hours or even longer, without the need of recharging the batteries, while still providing a system that measures the vital signs of patients in a reliable way.

One problem with the proposed system is that vital sign sensors, in particular optical vital sign sensors, are very sensitive to noise and movements. For example, when measuring heart rate and/or oxygen saturation on the basis of an optical measuring device, e.g. an opto-electronic device comprising one or more LEDS and photodiodes, small abrupt movements by a person in an "inactive state" (e.g. sitting or lying) may induce motion artefacts in the measured data, which make the data unreliable or even useless.

In high-care (intensive care) vital sign monitoring, it is known that movements of a patient are a dominant source for causing errors and deviations in the measured signal. High-care vital signs monitoring systems aimed at continuous real-time vital sign monitoring solve this problem by data processing techniques, e.g. by correcting (smoothing, averaging) and reducing noise artefacts that occur during the monitoring process. Such data processing techniques however require a substantial amount of processor resources and associated power consumption that is not compatible with the requirement that a low-care wireless measuring device should be a small wearable, low-power measuring device.

US2015/0157269 describes a measurement system for detecting a physiological signal based on an optical sensor for measuring SpO2 levels and a capacitive sensor for detecting motion of tissue. If the capacitive signal is above a certain threshold value, the system can disable the measurement of the optical sensor. A problem related to this prior art system is that tissue motion signal detected by the capacitive sensor may be a combination of different signals: blood movement within tissue, physical movement of tissue and/or changes in pressure/orientation of the capacitive sensor on the tissue. A separation of the tissue motion signal into the different individual signals requires data processing, leading to an estimate of the physical movement which is not very accurate. The capacitive sensor used in the system is not able to detect physical motion of a user in three dimensions. This way, not all movements are detected by the sensor so that the measurement system may start measuring optical signals while the user is moving. Further, the prior art system switches the optical sensor off whenever a motion level is detected that is above a certain threshold (e.g. one motion spike). Such scheme would disqualify measuring intervals in which an optical sensor signal could be measured that—for a large part—would be suitable for accurately deriving physiological parameters. Such scheme is not particular efficient in terms of power consumption.

Hence, from the above it follows that there is a need in the art for low-care vital sign monitoring schemes comprising wireless vital sign measuring devices that provide reliable, low-power data acquisition that is robust against noise, in particular against motion-induced noise.

SUMMARY OF THE INVENTION

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Functions described in this disclosure may be implemented as an algorithm executed by a microprocessor of a computer. Furthermore, aspects of the present invention may take the form of a computer program product embodied in one or more computer readable medium(s) having computer readable program code embodied, e.g., stored, thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber, cable, RF, etc., or any suitable combination of the foregoing. Computer program code for carrying out operations for aspects of the present invention may be written in any combination of one or more programming languages, including an object oriented programming language such as Java™, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor, in particular a microprocessor or central processing unit (CPU), of a general purpose computer, special purpose computer, or other programmable data processing apparatus to produce a machine, such that the instructions, which execute via the processor of the computer, other programmable data processing apparatus, or other devices create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts, or combinations of special purpose hardware and computer instructions.

It is an objective of the invention to reduce or eliminate at least one of the drawbacks known in the prior art.

The embodiments in this disclosure relate to the field of physiological monitoring and more specifically to a low-power, wireless wearable devices for measuring a trend of multiple vital signs in a cure setting, low care hospital ward. The embodiments include a system comprising low-power, wireless ear-worn sensors (measuring devices) for each patient, a central platform and a (mobile) user interface, specially focused on use by nurses and doctors in low care hospital wards. The wearable devices are configured to non-invasively measure multiple vital signs such as heart-rate, oxygen saturation, respiratory (breathing) rate, temperature, movement intensity, posture, sleep and many more.

In low-care general hospital wards, patients are promoted to get out of bed and start moving. Therefore, vital signs monitoring asks for comfortable, wireless sensors that are especially designed for these circumstances and can handle artefacts that stem from movement, external light and another external factors. On the other hand, the users (nurses primarily and doctors), ask for much simpler user interfaces and less (false alarms). Where doctors and nurses on an intensive care for example are continuously focussed on the monitors and are trained to interpret the data they see, on a general hospital ward, they should oversee data at a glance without being bothered with alarms that turn out to be false. They should be given vital sign information instead of raw data.

In low care hospital wards, reliable vital sign readings, ease of use for nurses, and the prevention of false alarms are more important than showing the most recent values, specific waveforms, and urgent alarms based on advanced settings. Therefore, advanced signal selection algorithms are used, to build long term trend information.

In contrast with continuous vital sign measurement systems as for example used in intensive-care applications known in the prior art, the embodiments in this disclosure include a vital sign measurement device configured for determining and providing reliable trend values in vital sign parameters wherein measured data are not corrected but selected using motion data generated by a motion sensor in the vital sign measurement device.

The embodiments include mobile vital sign measurement devices configured to detect artefacts in the measured signals and to reject parts of the measured signal that include these artefacts. Multiple selection and/or rejection algorithms may be used for signal selection. Therefore, only approved data are used so that only reliable vital sign values are reported. Hence, the invention aims to remove parts in the measured signal that are affected by noise, in particular by motion-induced noise, so that the sensor determines its vital sign parameters on the basis of "clean" sensor signals.

In an aspect, the invention relates to a method of determining one or more vital sign parameters by a vital-sign measurement device, preferably a wireless vital-sign measurement device, comprising: a motion sensor in the wireless measurement device measuring first motion information, preferably one or more first motion intensity values, of a user wearing the wireless measurement device, the measurement device being in an idle mode in which at least one opto-electronic sensor in the measurement device is deactivated; a processor in the wireless measurement device switching the measurement device in an active mode if the first motion information passes a first motion threshold, wherein in the active mode the at least one opto-electronic sensor is activated; during a measuring period, the at least one activated opto-electronic sensor exposing part of a skin tissue of the user to light, measuring one or more optical response signals associated with the exposed skin tissue and the motion sensor measuring second motion information, preferably one or more second motion intensity values, associated with movements of the user during the measuring period; the processor selecting or rejecting one or more pulses in the one or more optical response signals on the basis of the second motion information measured during the measuring period and determining one or more vital sign parameters on the basis of the one or more selected pulses.

Hence, in order to reliably determine one or more vital sign parameters the method includes data processing before and right after the optical response data that are needed for the vital sign measurement. Before starting the opto-electronic sensor a motion sensor, e.g. an accelerometer, is used to detect a moment with little or no movement to start measuring.

Then, after a predetermined measuring period, the measured optical response signals, in particular the pulses in the measured optical response signals, are analysed. This may be realized in various manners, e.g. by checking the patients' movement during the measuring of the signals and/or by comparing the morphology of the signal to a threshold, e.g. an ideal reference (wave) form. This morphologic analysis may be done using multiple parameters of this waveform. Part of these parameters may be based on a morphology per pulse, part may be based on similarities or variances between pulses. Then, when all checks are done, the signal is either accepted or rejected. Whenever accepted, vital signs can be calculated. Whenever rejected, a new measurement will be started.

This method guarantees 'always right' reported values. Accepted values will be reported on irregular times, based on both the set measurement intervals of the algorithm and the acceptance of the data selection. These discontinuous measurements may form the basis for the trend per vital sign parameter to be reported to a central server.

The measuring device may be ear-worn and small enough to be minimally incriminating for patients wearing the device for longer periods of time. Furthermore, the measuring device should be energy efficient so it can last on one charge of a small battery for a substantial period of time, e.g. at least 48 hours or more. This also puts a limitation on the choice of algorithms for the measurement protocol, data selection and vital sign calculation as all calculations done by the microprocessor will be energy consuming. To that end, the method according to the invention has an idle and an active state, wherein in the low-energy idle state, the opto-electronic sensor is deactivated and in the active state, the opto-electronic sensor is activated. This way, the energy consumption of the measuring device may be minimized.

In an embodiment, the method may further comprise: if the first motion information crosses a first motion threshold value, the processor starting a first restart timer for providing a first time delay; after the first time delay, the motion sensor measuring new first motion information and the processor switching the measurement device in an active mode if the new first motion information passes a first motion threshold. Hence, if the motion information measured by the motion sensor, e.g. an accelerometer, indicates that the motion intensity is too high, the measuring device will not activate the opto-electronic sensor in order to start a measuring period. Further, it will wait for a certain delay period before it starts measuring the motion intensity in order to determine whether it can activate the opto-electronic sensor.

In an embodiment, selecting or rejecting one or more pulses may comprise: comparing the second motion information associated with one or more pulses in the one or more optical response signals with a second motion threshold. In this embodiment, motion information, e.g. the motion intensity, of associated with the measured response signal use in order to select or reject parts, e.g. one or more pulses, of the measured response signal. This way, signal parts are selected that have a low probability that these signal parts are affected by motion noise.

In an embodiment, selecting or rejecting one or more pulses may comprise: determining one or more morphology characteristics of one or more pulses in the one or more optical response signals, preferably the morphology characteristics including at least one of: pulse length, amplitude or standard deviation; comparing at least one morphology characteristic of a pulse in the one or more optical response signals with a morphology threshold value. In this embodiment, the morphology of parts, e.g. one or more pulses, of the measured signal may be compared with morphology characteristics of a reference signal. If the deviations between morphology characteristics of the measured signal and reference signal are too large, these parts may be rejected as comprising artefacts.

In an embodiment, selecting or rejecting one or more pulses may comprise: determining one or more variations in one or more morphology characteristics of subsequent pulses in at least one optical response signal; comparing a variation in a morphology characteristic with a morphology variation threshold value. In this embodiment, the morphology between subsequent pulses in a measured signal may be compared so that if these deviations are too large, one or more pulses may be rejected.

In an embodiment, the method may further comprise: after the measuring period, the processor switching the measurement device to the idle mode. Thus, after measuring the optical response signals for a predetermined time, the measurement device may switch itself to a low-energy, idle mode in which the opto-electronic sensor and optionally other energy consuming electronic components are switched or in a low-energy mode.

In an embodiment, the method may further comprise: after determining the one or more vital sign parameters or after rejecting one or more pulses in the one or more optical response signals, the processor starting a second restart timer for providing a second time delay; after the second time delay, the motion sensor measuring new first motion information and the processor switching the measurement device in an active mode if the new first motion information passes a first motion threshold. Hence, after a full measurement cycle in which the processor may determine vital sign parameters on the basis of selected pulses in the optical response signal or in which the processor has rejected the pulses in the optical response signal, the measuring device wait for a certain delay period before it starts a new measurement cycle, by measuring the motion intensity in order to determine whether it can activate the opto-electronic sensor.

In an embodiment, determining one or more vital sign parameters may comprise: determining an oxygen saturation (SpO2) value in the blood and/or a heartbeat rate on the basis of the selected pulses.

In an embodiment, the measuring device may further comprise a temperature sensor. In an embodiment, during the predetermined measuring period, a temperature sensor may measure the temperature of the skin.

In an embodiment, the at least one opto-electronic sensor may comprise one or more light emitting devices, preferably one or more light-emitting diodes, for exposing part of a skin tissue of the user to light of one or more wavelengths and one or more light detecting devices, preferably one or more photodiodes, for measuring one or more optical response signals associated with the exposed skin tissue.

In an embodiment, the method may further comprise: the measurement device transmitting the one or more vital sign parameters to a computer that is configured to collect the vital sign parameters and determine a trend in the vital sign parameters associated with the user wearing the measuring device.

In an embodiment, the method may further comprise: associating time information, preferably a time-stamp, with the one or more vital sign parameters; storing the one or more vital sign parameters, the time information and, optionally, the second motion information in a buffer; and, transmitting the one or more vital sign parameters, the time information and, optionally, the second motion information in a message to a server.

In an embodiment, the measurement device may be configured as an ear-worn measuring device. In an embodiment, the ear-worn measuring device may comprise a resilient ear clamp for attaching the measuring device to the ear of the user.

In an embodiment, the measurement device may comprise a housing, the housing comprising a protrusion, the protrusion housing at least part of the opto-electronic sensor, wherein when attached the measuring device to the ear using the resilient ear clamp, the contact part of the protrusion is pressed against the back of the ear, preferably the posterior auricle of the ear.

In an embodiment, the wireless vital-sign measurement device may comprise: a motion sensor configured for measuring movement of the user wearing the measurement device and at least one opto-electronic sensor configured to expose part of a skin tissue of the user to light and measuring one or more optical response signals associated with the exposed skin tissue; a computer readable storage medium having at least part of a program embodied therewith; and, a computer readable storage medium having computer readable program code embodied therewith, and a processor, preferably a microprocessor, coupled to the computer readable storage medium, wherein responsive to executing the computer readable program code, the processor is configured to perform executable operations comprising: using the motion sensor to measure first motion information, preferably one or more first motion intensity values, of a user wearing the wireless measurement device, the measurement device being in an idle mode in which at least one opto-electronic sensor in the measurement device is deactivated; switching the measurement device in an active mode if the first motion information passes a first motion threshold, wherein in the active mode the at least one opto-electronic sensor is activated; during a predetermined measuring period, the at least one activated opto-electronic sensor exposing part of a skin tissue of the user to light and measuring one or more optical response signals associated with the exposed skin tissue and the motion sensor measuring second motion information, preferably one or more second motion intensity values, associated with movements of the user during the measuring period; and, selecting or rejecting one or more pulses in the one or more optical response signals on the basis of the second motion information measured during the measuring period and, optionally, if one or more pulses are selected by the processor determining one or more vital sign parameters on the basis of the one or more selected pulses.

In an aspect, the invention may relate to wireless vital-sign measurement device comprising: a processor; a motion sensor configured for measuring movement of the user wearing the measurement device; and, at least one opto-electronic sensor configured to expose part of a skin tissue of the user to light and measuring one or more optical response signals associated with the exposed skin tissue; wherein the processor is configured to: activate the at least one opto-electronic sensor in order to expose part of a skin tissue of the user to light and measuring, during a predetermined measuring period, one or more optical response signals associated with the exposed skin tissue, wherein the opto-electronic sensor is activated on the basis of motion information measured by the motion sensor before the opto-electronic sensor was activated; and, select or reject one or more pulses in the one or more optical response signals on the basis of motion information measured by the motion sensor during the measuring period and/or on the basis of one or more morphology characteristics of one or more pulses in the one or more optical response signals; and, if one or more pulses are selected, determining one or more vital sign parameters on the basis of the one or more selected pulses.

In a further aspect, the invent wireless ear-wearable vital-sign measurement device comprising: a processor, a motion sensor configured for measuring movement of the user wearing the measurement device; and, at least one opto-electronic sensor configured to expose part of a skin tissue of the user to light and measuring one or more optical response signals associated with the exposed skin tissue; the measurement device comprising a housing for housing the processor, the motion sensor and the opto-electronic sensor, and an resilient ear clamp for attaching the measuring device to the ear of the user, the housing comprising a protrusion, the protrusion housing at least part of the opto-electronic sensor, wherein, when the measuring device is attached to the ear using the ear clamp, the contact part of the protrusion is pressed against the part of the ear of the user, preferably part of the back of the ear of the user.

In yet a further aspect, the invention may relate to a method of determining one or more vital sign parameters by a vital-sign measurement device, preferably a wireless vital-sign measurement device, comprising: a motion sensor in the measurement device measuring first motion information, preferably one or more first motion intensity values, of a user wearing the wireless measurement device, the measurement device being in an idle mode in which at least one opto-electronic sensor in the measurement device is deactivated; a processor in the measurement device switching the measurement device in an active mode if the first motion information passes a first motion threshold, wherein in the active mode the at least one opto-electronic sensor is activated; during a predetermined measuring period, the at least one activated opto-electronic sensor exposing part of a skin tissue of the user to light and measuring one or more optical response signals associated with the exposed skin tissue. Hence, in this embodiment, the activating the opto-electronic sensor, a motion sensor, e.g. an accelerometer, is used to detect a moment with little or no movement to start measuring. The opto-electronic sensor is only activated if the user is not moving or at least moving with an intensity that does not significantly affect the optical response signal. This way, the energy consumption of the measuring device can be reduced while at the same time the risk that the measured optical response signal is affected by motion noise can be significantly reduced.

In an embodiment, the method may include: the processor selecting or rejecting one or more pulses in the one or more optical response signals on the basis of morphology characteristics of one or more pulses and, optionally, if one or more pulses are selected by the processor determining one or more vital sign parameters on the basis of the one or more selected pulses.

The invention is also directed to a computer program product comprising software code portions configured for, when run in the memory of a computer, executing the method steps according to any of claims as described above.

The invention will be further illustrated with reference to the attached drawings, which schematically will show embodiments according to the invention. It will be understood that the invention is not in any way restricted to these specific embodiments.

BRIEF DESCRIPTION OF THE DRAWINGS

FIG. 6A-6C depict clamping a sensor compartment of an ear-wearable measuring device according to an embodiment of the invention to an ear.

DETAILED DESCRIPTION

The embodiments in this disclosure described low-care wireless vital sign monitoring systems and wireless low-power vital sign measuring devices for use in such systems. The wireless vital sign measuring devices provide accurate determination of vital sign parameters for use in low-care vital sign monitoring. The measuring devices are adapted to provide low-power data acquisition and reliable determination of vital sign parameters, which are robust against noise, in particular against motion-induced noise.

Figure 1A:
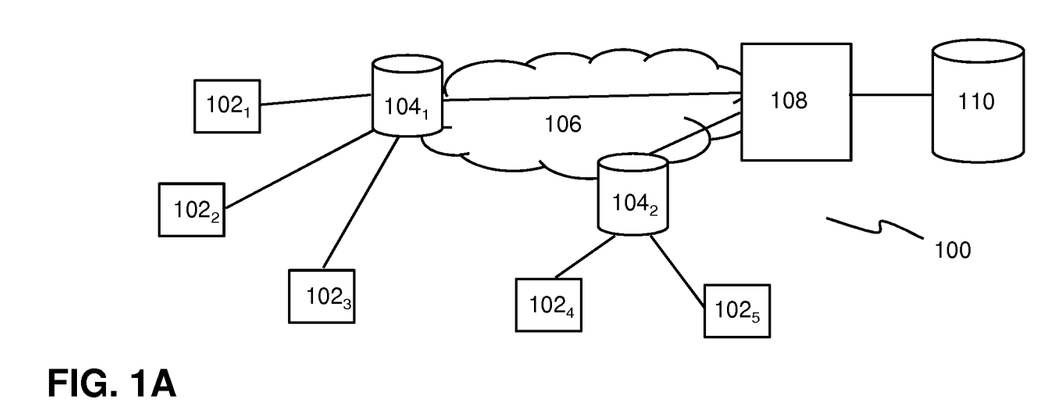
FIGS. 1A and 1B depict schematics a low-care vital sign monitoring system comprising a plurality of wireless vital sign measuring devices according to an embodiment of the invention.
Figure 1B:
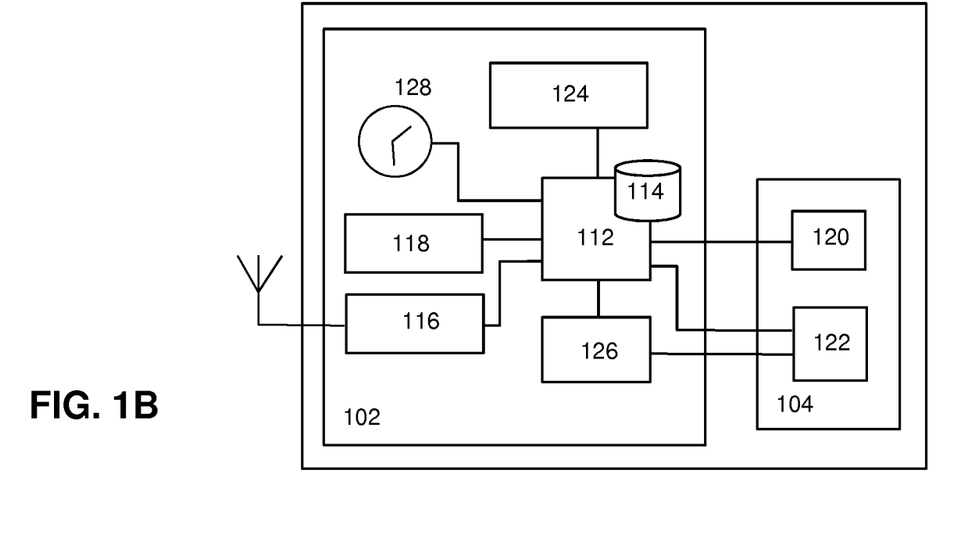

FIGS. 1A and 1B depict schematics a low-care vital sign monitoring system and a wireless vital sign measuring device for use in such monitoring system according to various embodiments of the invention. In particular, FIG. 1A depicts a low-care vital sign monitoring system 100 comprising a plurality of wireless vital sign measuring devices $102_{1-5}$ (hereafter in short also referred to as measuring devices) that are configured to wirelessly communicate with one or more base stations $104_{1,2}$. A base station may be configured to receive data from different measurement devices that are located within a certain distance from the base station.

A measuring device may include one or more sensors that are in contact with or in close vicinity to the skin of a person wearing the measuring device so that the sensors can measure characteristics, e.g. an optical response and/or temperature, of the skin tissue. Additionally, one or more sensors, e.g. an accelerometer, may be configured to generate motion information associated with the movements of the person wearing the measuring device and/or posture information associated with the posture of the person wearing the measuring device.

At predetermined (measuring) time instances the measuring device determines one or more vital sign parameters, e.g. heartbeat, oxygen saturation (Spo2), temperature, posture, etc. of the person wearing the measuring device. The measuring time instances may be periodically (every N minutes or every N hours or the like), a-periodically (e.g. depending on certain conditions) or a combination thereof.

The measurement device may process signals generated by the sensors (sensor signals) on the basis of motion data that are measured during the measuring the data that are used for determining the vital sign parameters. The thus processed sensor signals may be used to calculate one or more vital sign parameters. The vital signal parameters may be temporarily stored before transmitting the parameters in one or more messages via a wireless interface, e.g. a radio interface, to a base station. A central computer 108 may be connected via one or more networks 106 to the base stations of the vital sign measuring system may receive the vital sign parameters and monitor the measured parameters of different patients in time.

The monitoring process may include determining a trend of one or more vital sign parameters and triggering a warning signal in case at least one of the vital sign parameters (or the trend of at least of the vital sign parameters) indicates a (substantial) deterioration of at least one of the vital sign parameters (or trend therein).

FIG. 1B depicts a wireless vital sign measuring device according to an embodiment of the invention. In particular, FIG. 1B depicts a schematic of a wireless vital sign measuring device 102 which may comprise an electronics compartment 112 and a sensor compartment 104. The measuring device may comprise a microprocessor 112 coupled to a memory 114, a rechargeable battery 124, a wireless radio interface 116 (Bluetooth, ZigBee, Wi-Fi, etc.) and one or more sensors. Examples of such sensors include (but are not limited to) a motion sensor 118 (e.g. a digital accelerometer), a temperature sensor 120 and at least one opto-electronic sensor 122. The output of the one or more sensors may be fed into the input of an analog front-end 126, e.g. a low-noise amplifier, so that sensor signals can be amplified before they are processed by the microprocessor. At regular intervals, the sensors may be activated on the basis of a motion signal of the motion detector, sensor signals may be accepted or rejected on the basis of a motion signal and accepted sensor signals may be processed in order to determine vital sign parameters such as SpO2 level, hear beat rate, temperature and motion associated with a particular time instance. The determined vital sign parameters may be time stamped on the basis of a clock 128, stored in the memory 114 and transmitted at regular intervals to a base station.

At least part of the vital sign parameters may be derived from pulse oximetry, which is a non-invasive method for monitoring a person's oxygen saturation. A blood-oxygen saturation reading indicates the percentage of hemoglobin molecules in the arterial blood which are saturated with oxygen. The term SpO2 means the SaO2 measurement determined by pulse oximetry.

An SpO2 sensor is an opto-electronic sensor including one or more light emitting devices, e.g. LEDs, adapted to emit light of a predetermined wavelength or a predetermined band of the electro-magnetic spectrum onto a tissue and one or more light sensors, e.g. photodiodes, adapted to receive LED light that is reflected from the tissue or transmitted through tissue. In particular, light emitting diodes may expose part of the tissue to red and infrared light and one or more light detectors, e.g. a photodiode, may.

In an embodiment, for example, the motion sensor may be an accelerometer, typically a low power digital accelerometer, that is adapted to continuously measure (e.g. at a rate 1-50 Hz) the motion in three dimensions, e.g. a motion vector having components in the x,y,z direction.

The amount of light received by the detector provides an indication of the amount of oxygen bound to the hemoglobin in the blood. Oxygenated hemoglobin (oxyhemoglobin or HbO2) absorbs more infrared light than red light and deoxygenated hemoglobin (Hb) absorbs more red light than infrared light. Thus, by detecting the amount of red and infrared light transmitted through or reflected from the tissue an SpO2 value may be determined.

Because the amount of oxygen-rich arterial blood that is present in the arteries varies in accordance with the heartbeat, the measured signals are pulsed signals. Examples of the signals will be described hereunder with reference to FIG. 3A-3C.

An SpO2 sensor may be attached to a body part having relatively translucent skin tissues, typically to an extremity of a body part such as a finger, toe or ear. Further, in contrast to high-care applications, in low-care applications, a user is not bound to bed but should be able to walk around and move freely. Hence, for that reason, the measuring device may be configured as a small wireless wearable device that is in contact with a part of the skin. As will be described hereunder in more detail, in an embodiment, the measuring device may be configured as an ear-worn wireless measuring device wherein the measuring device comprises an opto-electronic sensing part that is in contact with the skin of (the back of) an ear of the person wearing the measuring device.

In order to control the power consumption, the measurement device can switch between an idle state and an active state. In the idle state, the opto-electronic sensor is in a low-power (sleeping) state, wherein the opto-electronic sensor is deactivated. In contrast, the low-power motion sensor is still active so that it can generate motion information that can be used by the processor to switch the measuring device to the active state in which the opto-electronic sensor is activated so that during a predetermined period of time optical data can be measured. Once the measurement period is over, the processor may switch back to the idle state.

Hence, the low-power motion sensor may continuously or at least regularly or periodically measure the motion of the patient wearing the measuring device wherein the motion information may be used to switch the measuring device from a idle state to an active state, wherein the opto-electronic sensor is activated and wherein the processor may decide to activate the wireless interface in order to transmit at least part of the measured data to a base station.

As will be described hereunder, the control of the idle and active state of the measuring device by motion information results in a low-power data acquisition process that enables selection of "clean" optical sensor response signals, i.e. an optical response signal that is not or at least little affected by movements of the user that can be used for determining reliable vital sign parameters.

Figure 2:
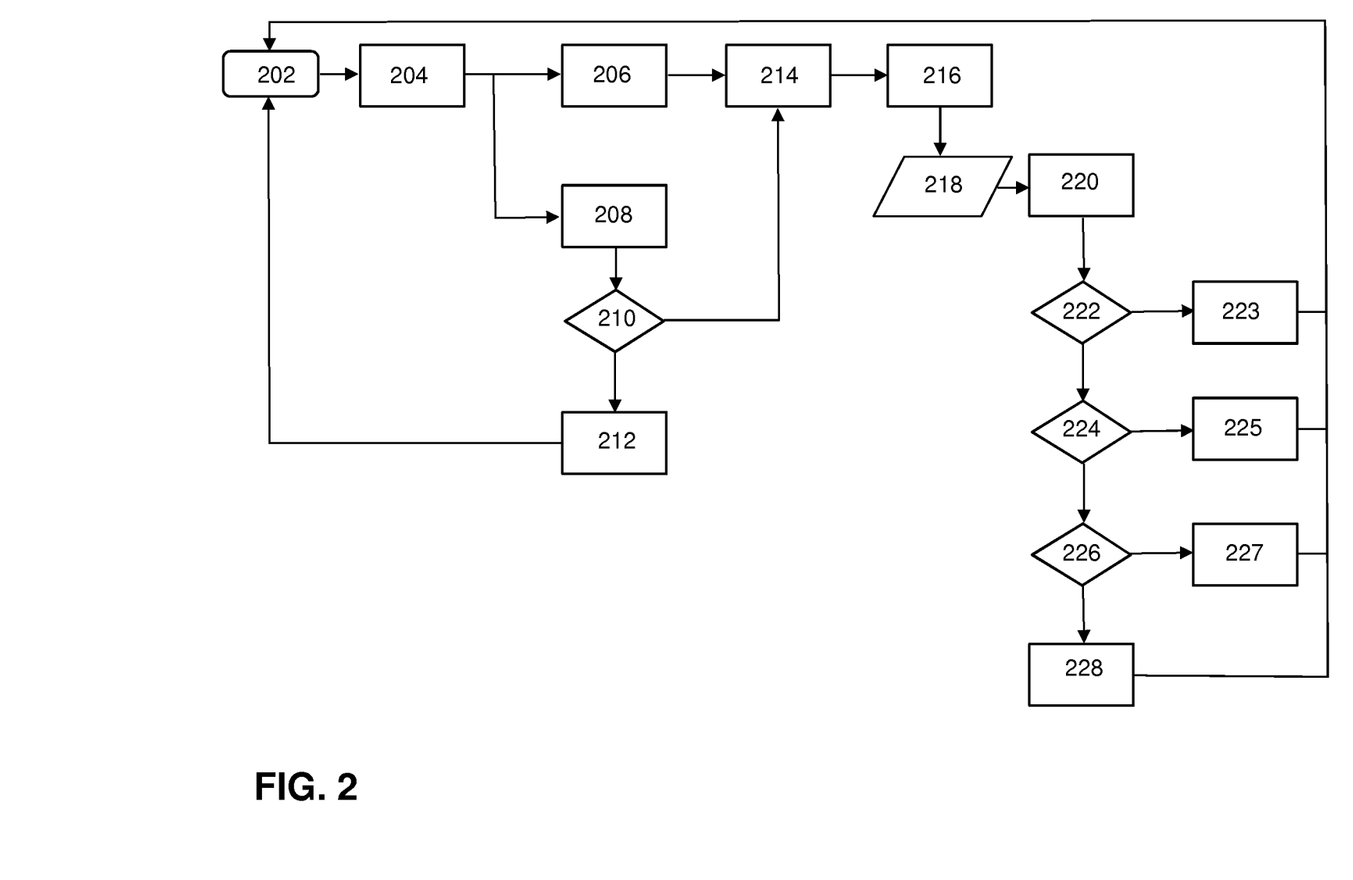
FIG. 2 depicts a high-level flow chart of a low-power data acquisition and processing method according to an embodiment of the invention.

FIG. 2 depicts a high-level flow chart of a low-power data acquisition and processing method according to an embodiment of the invention. In particular, FIG. 2 depicts a high-level flow chart of a low-power data acquisition and processing method for use in vital sign measuring devices as described with reference to FIGS. 1A and 1B. The method may be executed by a processor in the measuring device and may be implemented as one or more software modules, hardware modules or a combination thereof.

The method of FIG. 2 may start with a measuring device in an idle state receiving in a first step 202 a trigger to start a measurement cycle. In response to the trigger, the input of the processor may receive motion data, i.e. data generated by the motion sensor (step 204).

The processor may (periodically) buffer motion data for a predetermined time period (e.g. 1-5 seconds) and calculate motion information. The motion information may include one or more values that are representative for the motion intensity, an average motion and/or a motion variation. The motion intensity may e.g. be determined using the magnitude of the motion vector which may be determined by the square root of the sum of the squares of the motion in the x,y,z direction (step 208).

On the basis of the motion information the processor may determine whether or not to switch from the idle to the active state in order to enable the opto-electronic sensor measure optical data. For example, in an embodiment, the processor may determine that the motion information is smaller or larger than a predetermined motion threshold value (step 210). The processor may switch the measuring device to the active state if the motion information is smaller than the predetermined motion threshold value (step 214).

If the motion information is larger than the motion threshold value, the processor may decide to not switch to the active state and start a restart timer which provides a time delay (step 212), e.g. 5-30 seconds, before a new measurement cycle is triggered (including the buffering of new motion data, determining motion information and the checking whether the motion information is below or above a certain threshold as described above with reference to steps 202-208).

Figure 3A:
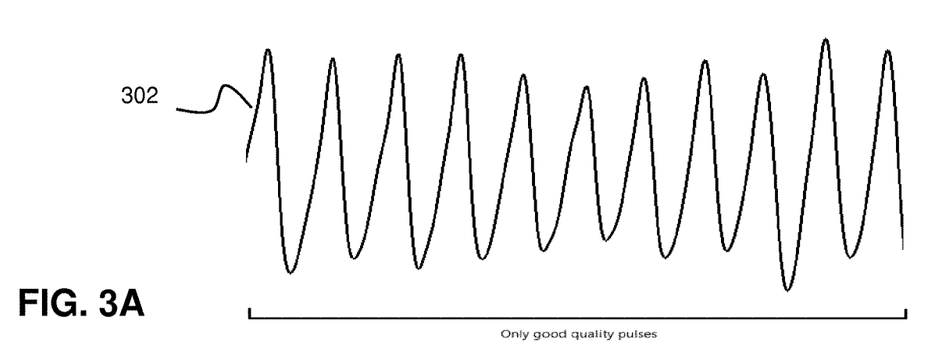
FIG. 3A-3C illustrate the signal degradation induced by motion.
Figure 3B:
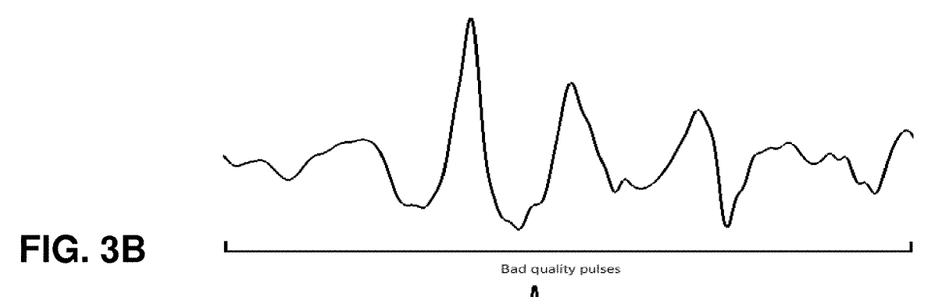
Figure 3C:
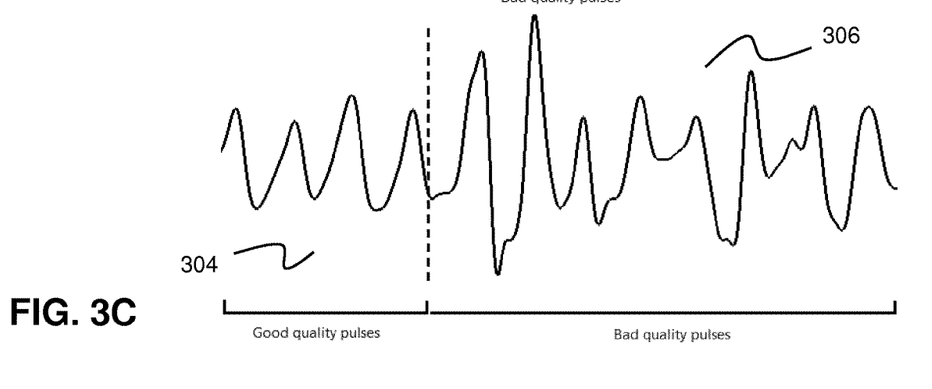

Hence, the processor uses the motion information obtained on the basis of motion data that are measured during the measurements of the optical data in order to determine the degree of degradation of the optical data by motion of the user. Illustration of the signal degradation by motion are provided in FIG. 3A-3C. FIG. 3A depicts an example of a "clean" pulsed optical response signal of the opto-electronic sensor of the measuring device that is measured during a period wherein the user does not move or is making movements with so low intensities that it does not affect the optical sensor signal. In contrast, FIG. 3B depicts an example wherein whole optical response signal is severely degraded by movements or other noise sources thereby making the measurements not suitable for reliable determination of vital sign parameters. FIG. 3C depicts an example wherein only part of the signal is affected by movements, e.g. because the user started to move during the measurements. In that case, only part of the signal can be used for determining reliable vital sign parameters.

In an embodiment, if the measuring device is switched into the active state, the processor may determine whether the measuring device is correctly positioned and attached to the skin tissue so that it can be determined that the response signal originates from the tissue (step 216). This way, the processor may run a test algorithm in order to determine whether the opto-electronic sensor provides a response that can be identified as a response that is characteristic for tissue so that the measuring device is able to check whether it is correctly positioned. Additionally, the processor may determine optimum light intensity values for the light sources (e.g. LEDs) of the opto-electronic sensor. These light intensity vales may be used by the opto-electronic sensor during a measurement cycle.

If the test algorithm determines that the test response of the sensor is correct, the measuring of the optical sensor data may start. For example, the processor may start measuring the optical response signal that is sensed by the opto-electronic sensor for a predetermined measuring period wherein during the measuring process of the optical data, associated motion data are also measured by the motion sensor (step 218). The obtained optical sensor data and the motion data may be buffered in a memory of the measuring device.

Once sufficient data a buffered, the processor may switch the measurement in the low-power idle mode and execute a signal selection process (step 220). The signal selection process may select optical data on the basis of the motion data that was measured during the period that the optical data was measured. Further, the signal selection process may include determining morphology characteristics of one or more measured pulses in the optical data. The measured motion information and the determined morphology characteristics may be compared with one or more threshold values in order to determine whether the measured data are acceptable for further data processing, which may include determining a heartbeat rate and/or an SpO2 value on the basis of the measured optical data. The signal selection process will be described hereunder in greater detail with reference to FIG. 4.

The outcome of the signal selection process may be a "reject" or an "accept". For example, if the motion information indicates that the motion during the measurement of the optical data was too high over the whole period, the optical data may be rejected right away. Alternatively, if the motion during the measurement of the optical data indicates that the motion was only to high during one or a few pulses, in that case, —if the morphology characteristics indicate that the variations are within certain limited—at least part of the measured optical data may be accepted for further processing.

The processor may determine when to start a new measurement cycle depending on the outcome of the selection process (step 222). If the output of the signal selection process indicates that measured data are accepted, the processor may determine to wait for a predetermined time before starting a new measurement cycle. To that end, the processor may trigger a delay timer of a predetermined first delay period, e.g. 5 minutes (step 223). Once the delay timer has reached the end of the first delay period the processor may start a new measurement cycle.

Similarly, if the signal selection process in step 222 indicates that the measured data are rejected, the processor may determine to wait for a predetermined time before starting a new measurement cycle. In that case, the processor may control the length of the delay period as a function of certain conditions. For example, the length of the delay period may dependent on the number of consecutive rejects. This is shown in steps 224-228 of the process of FIG. 2.

If the outcome of the signal selection process (step 222) is a reject, the processor may determine whether the data of the previous measurement cycle were rejected too (step 224). If that is the case the delay time may be set of a second delay period (step 225) that is different from the first delay period (i.e. the delay period which is set when the outcome of the signal selection process is accepted). For example, when a first reject has been determined, then the delay timer may be set to a one-minute time delay before a new measurement cycle is trigged. If the processor determines that the reject is the second consecutive reject (step 226), the processor may set the delay timer to a third delay period that is longer when compared to second delay period, e.g. a delay of two minutes instead of one minute (step 227). If the reject is the third consecutive reject (or more) yet another delay period may be set that may be different from the first and second delay period.

Figure 4:
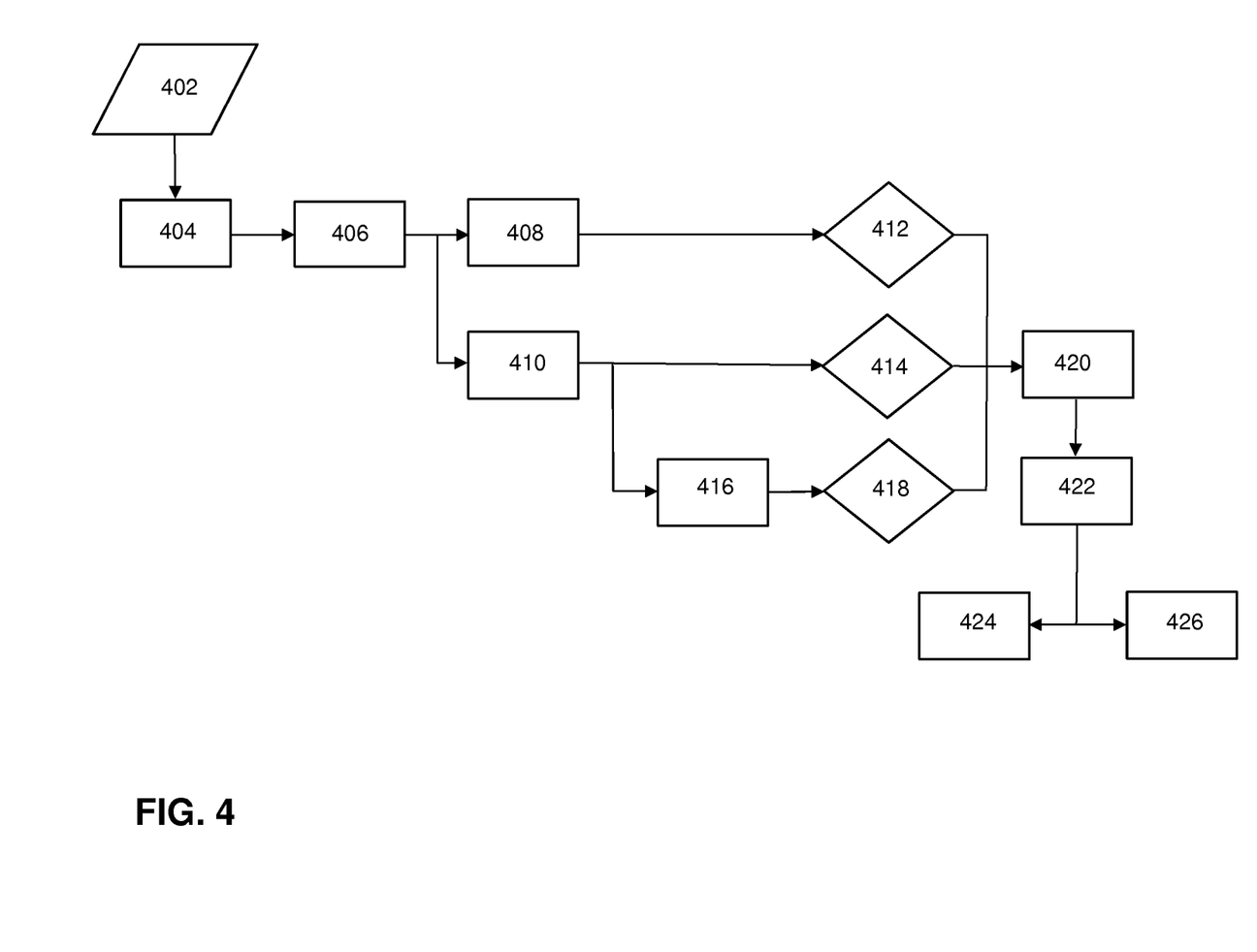
FIG. 4 depicts a flow chart of a sign signal selection method according to an embodiment of the invention.

FIG. 4 depicts a flow chart of a signal selection method according to an embodiment of the invention. The method may be executed by the processor of the measurement and may start with the reception of a set of optical data (step 402) representing optical response signals which are measured within a predetermined time window. The processor may further receive motion information representing the motion of the user during the measuring of the optical data set. Before analysing the optical response signals, the processor may pre-process the data (step 404), including high and low-pass filtering, normalization of measured values, etc. Thereafter, the processor may determine the pulses of each optical response signal (step 406) and calculate motion information, in particular the motion intensity per pulse (step 408). Further, the processor may determine the morphology characteristics of each pulse (step 410). The morphology characteristics may include pulse length, amplitude, standard deviation, etc.

Thereafter, for each pulse the processor may compare the motion information associated with a pulse with a motion threshold (step 412). Similarly, for each pulse the processor may compare each of the pulse characteristics with a pulse characteristic threshold (step 414). Additionally, in an embodiment, the processor may determine the variation of one or more morphology characteristics between neighboring pulses in an optical response signal (step 416) and compare the calculated variations with a pulse characteristics variation threshold (step 418).

Based on the outcome of the comparison steps, the pulses may be classified (step 420) in pulses that are not or only little degraded by the movements of the user (and thus suitable for determining vital sign parameters) and pulses that are degraded by the movements of the user (and thus not suitable for determining vital sign parameters). If there are no suitable pulses classified or if the amount of suitable pulses is not enough for determining reliable vital sign parameters then the processor rejects the set of optical data. If a sufficient amount of suitable pulses are classified than the processor may then select at least part of the pulses that are classified as being suitable and use these pulses for reliably determining vital sign parameters. For example, the selected pulses may be fed to the input of one or more well-known algorithms for determining information on the arterial oxygen saturation (SpO2) in the blood and for determining an heartbeat rate.

Vital sign parameters may be stored in the memory of the measuring device, along with time information (e.g. a time stamp) indicating the time the parameters were determined. Thereafter, the processor may repeat the process as described with reference to FIG. 2-4 unit the processor decides to wirelessly send an amount of vital sign parameters in a message to a base station.

Figures 5, 6:
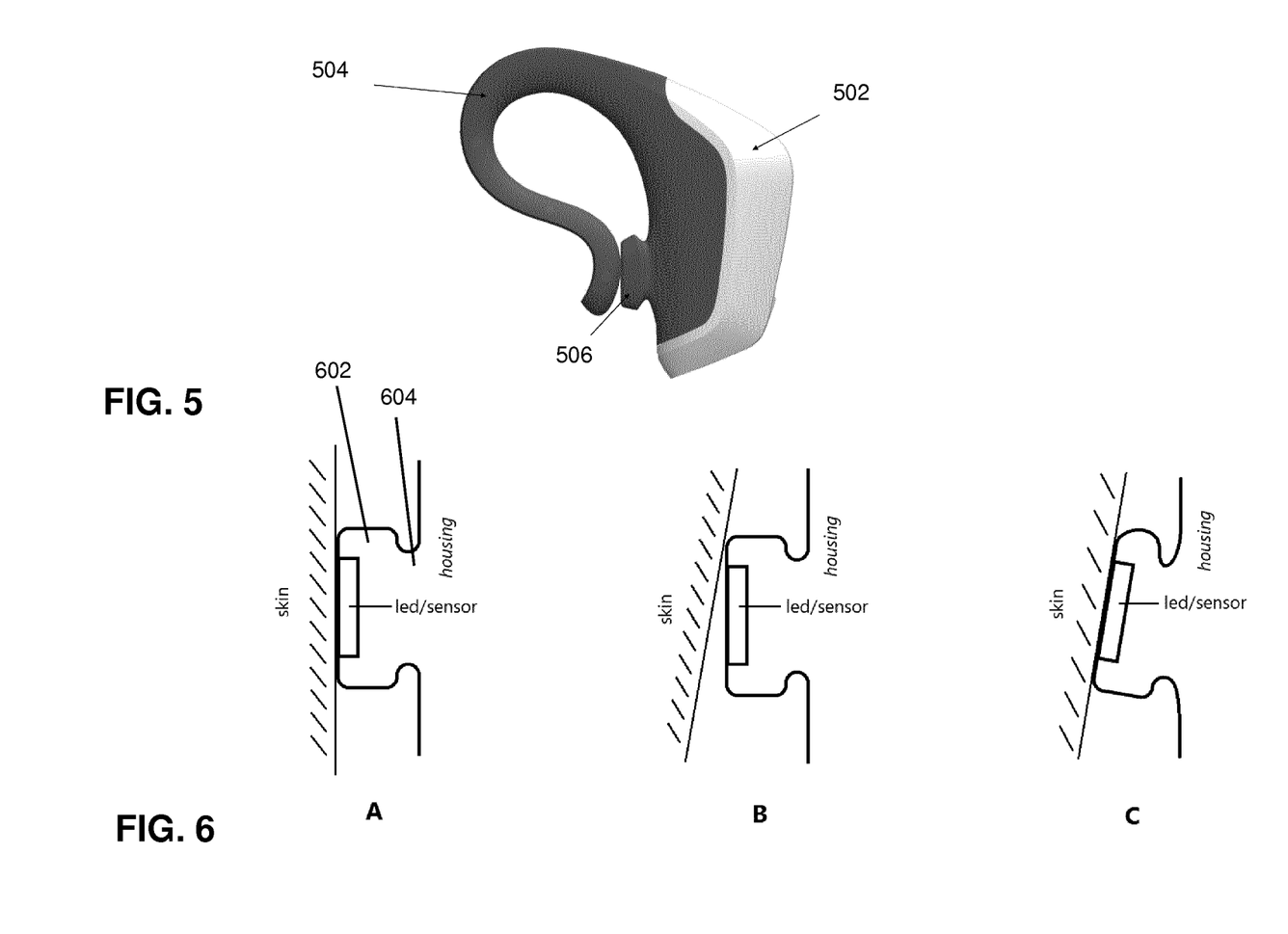
FIG. 5 depicts an example of an ear-wearable measuring device according to an embodiment of the invention.

FIG. 5 depicts an example of an ear-worn measuring device according to an embodiment of the invention. The measuring device comprises a housing comprising an electronics compartment 502. A resilient ear clamp 504 is connected to the housing or formed as part of the housing. The housing further comprises a sensor compartment 506 for housing the one or more sensors, or at least the parts of the one or more sensors that need to be in close contact with the skin tissue (e.g. the opto-electronic sensor and, optionally, a temperature sensor. The sensor compartment may be configured in the form of at least one protrusion that is resiliently connected to the housing of the electronics. The ear clamp may be shaped in accordance with the human ear so that when attaching the measuring device to the ear using the ear claim, the clamping action of the ear clamp will position and press a surface of the sensor compartment to the skin of (part of) the ear, in particular the back of the ear.

FIG. 6A-6C depict clamping a sensor compartment of an ear-wearable measuring device according to an embodiment of the invention to an ear. In particular FIG. 6A depicts a cross-sectional schematic of a sensor compartment that is resiliently connected to the housing of the measuring electronics. The sensor compartment has the form of a protrusion comprising a contact part 602 and a base part 604. Due to the claiming action the contact part of the sensor compartment is pressed against the skin, e.g. the back of the ear, of the user wearing the sensor so that good contact between the sensor and the skin is established.

The resilient protrusion-shaped sensor compartment decreases the risk of sub-optimal contact between optical sensor and the skin, especially when skin surface and the surface of the sensor compartment are not aligned as shown in FIG. 6B. Due to the resilient properties of the sensor compartment, the clamping action of the clamping action of the ear clamp will position and press the contact part of the sensor compartment to the skin of (part of) the ear regardless of the relative orientation of the (top) surface of the sensor compartment and the skin. As shown in FIG. 6C, the clamping action will slightly deform the contact part and the base part. Further, by making the dimensions of the base smaller than the contact part, the contact part may bend easily in any desired direction. This way, good optical contact is guaranteed for different ear shapes and sizes.

Figure 7:
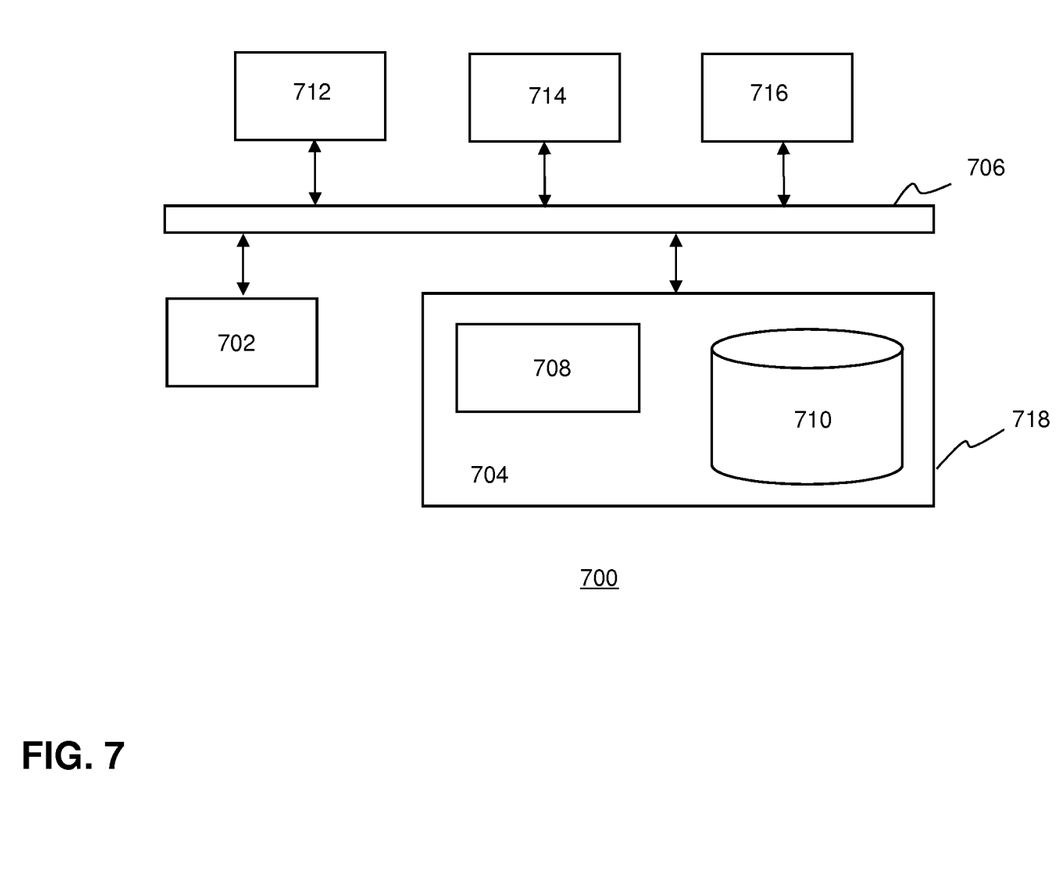
FIG. 7 depicts a block diagram illustrating an exemplary data processing system that may be used with embodiments described in this disclosure.

FIG. 7 is a block diagram illustrating an exemplary data processing system that may be used in as described in this disclosure. Data processing system 700 may include at least one processor 702 coupled to memory elements 704 through a system bus 706. As such, the data processing system may store program code within memory elements 704. Further, processor 702 may execute the program code accessed from memory elements 704 via system bus 706. In one aspect, data processing system may be implemented as a computer that is suitable for storing and/or executing program code. It should be appreciated, however, that data processing system x00 may be implemented in the form of any system including a processor and memory that is capable of performing the functions described within this specification.

Memory elements 704 may include one or more physical memory devices such as, for example, local memory 708 and one or more bulk storage devices 710. Local memory may refer to random access memory or other non-persistent memory device(s) generally used during actual execution of the program code. A bulk storage device may be implemented as a hard drive or other persistent data storage device. The processing system 700 may also include one or more cache memories (not shown) that provide temporary storage of at least some program code in order to reduce the number of times program code must be retrieved from bulk storage device 710 during execution.

Input/output (I/O) devices depicted as input device 712 and output device 714 optionally can be coupled to the data processing system. Examples of input device may include, but are not limited to, for example, a keyboard, a pointing device such as a mouse, or the like. Examples of output device may include, but are not limited to, for example, a monitor or display, speakers, or the like. Input device and/or output device may be coupled to data processing system either directly or through intervening I/O controllers. A network adapter 716 may also be coupled to data processing system to enable it to become coupled to other systems, computer systems, remote network devices, and/or remote storage devices through intervening private or public networks. The network adapter may comprise a data receiver for receiving data that is transmitted by said systems, devices and/or networks to said data and a data transmitter for transmitting data to said systems, devices and/or networks. Modems, cable modems, and Ethernet cards are examples of different types of network adapter that may be used with data processing system 750.

As pictured in FIG. 7, memory elements 704 may store an application 718. It should be appreciated that data processing system 700 may further execute an operating system (not shown) that can facilitate execution of the application. Application, being implemented in the form of executable program code, can be executed by data processing system 700, e.g., by processor 702. Responsive to executing application, data processing system may be configured to perform one or more operations to be described herein in further detail.

In one aspect, for example, data processing system 700 may represent a client data processing system. In that case, application 718 may represent a client application that, when executed, configures data processing system 700 to perform the various functions described herein with reference to a "client". Examples of a client can include, but are not limited to, a personal computer, a portable computer, a mobile phone, or the like.

In another aspect, data processing system may represent a server. For example, data processing system may represent an (HTTP) server in which case application 718, when executed, may configure data processing system to perform (HTTP) server operations. In another aspect, data processing system may represent a module, unit or function as referred to in this specification.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention claimed is:

1. A wireless, ear-worn vital-sign measurement device comprising:
 a processor;
 an accelerometer configured for measuring movement of a user wearing the measurement device in three dimensions;
 an opto-electronic sensor comprising a light emitting device configured to expose part of a skin tissue of a user to light and a light detection device for measuring one or more optical response signals reflected back from the exposed skin tissue;
 a resilient ear clamp for attaching the measuring device to the ear of the user; and
 a housing for housing the processor and the accelerometer, the housing comprising a resilient protrusion, the resilient protrusion comprising a base part that is resiliently connected to a contact part which houses the light emitting device and the light detection device;
 dimensions of the base part being smaller than dimensions of the contact part, so that, when pressed against a backside of an ear of the user, the contact part bends in an angular direction relative to the base part and the contact part deforms so that the light emitting device and the light detection device are pressed against the backside of the ear;
 wherein the processor is configured to:
 activate the opto-electronic sensor in order to expose part of a skin tissue of the user to light and measuring, during a predetermined measuring period, at least one optical response signal associated with the exposed skin tissue, the response signal comprising a plurality of pulses, wherein the opto-electronic sensor is activated on the basis of first motion information measured by the accelerometer before the opto-electronic sensor was activated;
 selecting or rejecting a pulse in the at least one optical response signal based on second motion information associated with the plurality of pulses as measured by the accelerometer during the measuring period and/or on the basis of one or more morphology characteristics of the pulse; and,
 if one or more pulses are selected, determining one or more vital sign parameters based on the one or more selected pulses.

2. An ear-worn vital-sign measurement device comprising:
 a processor,
 an opto-electronic sensor comprising a light emitting device configured to expose part of a skin tissue of a user to light and a light detection device for measuring one or more optical response signals reflected back from the exposed skin tissue;
 a housing for housing the processor, the housing comprising a compartment in the form of a resilient protrusion for housing the light emitting device and the light detection device, the resilient protrusion comprising a base part which is resiliently connected to a contact part which houses the light emitting device and the light detection device, and a top surface of the contact part being configured as a contact surface for contacting the skin tissue;
 a resilient ear clamp connected to the housing for attaching the measurement device to the ear of the user,
 the base part being resiliently connected to the housing of the processor, and dimensions of the base part being smaller than dimensions of the contact part, so that when the measurement device is attached to the ear using the ear clamp, a clamping action of the ear clamp bends the contact part in an angular direction relative to the base part and deforms the contact part so that the light emitting device and the light detection device are pressed against a part of a back of the ear of the user.

3. The vital-sign measurement device according to claim 2 wherein the measurement device is a wireless measurement device.

4. The wireless vital-sign measurement device according to claim 1, wherein the morphology characteristics include at least one of pulse length, amplitude and standard deviation.

5. The wireless vital-sign measurement device according to claim 1, wherein determining one or more vital sign parameters comprises:
 determining an oxygen saturation ($SpO_2$) value in the blood and/or a heartbeat rate based on the selected pulses.

6. The wireless vital-sign measurement device according to claim 1, further comprising:
 after the measuring period, the processor switching the measurement device to an idle mode.

* * * * *